United States Patent
Bhat et al.

(10) Patent No.: US 9,940,713 B1
(45) Date of Patent: Apr. 10, 2018

(54) MR-BASED NAVIGATORS FOR INTER-SCAN AND INTRA-SCAN MOTION CORRECTION

(71) Applicants: Siemens Healthcare GmbH, Erlangen (DE); The General Hospital Corporation, Boston, MA (US)

(72) Inventors: Himanshu Bhat, Newton, MN (US); Keith Aaron Heberlein, Charlestown, MA (US); Thomas Beck, Erlangen (DE); Martin Harder, Nürnberg (DE); Andre Jan Willem Van Der Kouwe, Woburn, MA (US); Matthew Dylan Tisdall, Somerville, MA (US)

(73) Assignees: Siemens Healthcare GmbH, Erlangen (DE); The General Hospital Corporation, Boston, MA (US)

( * ) Notice: Subject to any disclaimer, the term of this patent is extended or adjusted under 35 U.S.C. 154(b) by 0 days.

(21) Appl. No.: 15/351,471

(22) Filed: Nov. 15, 2016

(51) Int. Cl.
| G06T 7/00 | (2017.01) |
| A61B 5/055 | (2006.01) |
| G01R 33/565 | (2006.01) |
| G01R 33/3875 | (2006.01) |
| G06T 7/70 | (2017.01) |
| A61B 5/00 | (2006.01) |

(52) U.S. Cl.
CPC .......... G06T 7/0012 (2013.01); A61B 5/0037 (2013.01); A61B 5/055 (2013.01);
(Continued)

(58) Field of Classification Search
CPC ...................... G06T 7/0012; G06T 7/70; G06T 2207/30204; G06T 2207/30004; G06T 7/74; G06T 7/0081; G06T 2207/10088; G01R 33/3875; G01R 33/56509; G01R 33/48; G01R 33/34; A61B 5/055; A61B 5/721; A61B 5/1127; A61B 5/1128;
(Continued)

(56) References Cited

U.S. PATENT DOCUMENTS

| 5,539,312 A * | 7/1996 | Fu ..................... G01R 33/56509 |
| | | 324/309 |
| 6,184,682 B1 * | 2/2001 | Ehman .................... G06T 5/003 |
| | | 324/300 |

(Continued)

FOREIGN PATENT DOCUMENTS

DE  WO 2013118040 A1 *  8/2013  ......... G01R 33/4828

*Primary Examiner* — Manav Seth

(57) ABSTRACT

A method for MRI inter-scan motion correction includes performing (i) an anatomical localizer scan of a region of interest (ROI) to identify anatomical landmarks defining orientation of a surrounding field-of-view (FOV); (ii) an inter-scan motion reference scan of the ROI to acquire a reference inter-scan dataset indicating a reference navigator location in the ROI; and (iii) scans of the ROI to acquire k-space data. Prior to one or more of the scans, a motion correction process is performed that includes (a) performing an inter-scan motion tracking scan to acquire a tracking inter-scan dataset indicating an updated reference navigator location; (b) determining an estimation of inter-scan patient motion based on a comparison between the reference inter-scan and tracking inter-scan datasets; and (c) updating the FOV relative to the landmarks based on that estimation. Images of the ROI may be generated using the k-space data acquired with each of the scans.

21 Claims, 6 Drawing Sheets

(52) U.S. Cl.
CPC ... *G01R 33/3875* (2013.01); *G01R 33/56509* (2013.01); *G06T 7/70* (2017.01); *G06T 2207/10088* (2013.01); *G06T 2207/30204* (2013.01)

(58) Field of Classification Search
CPC ............ A61B 5/0037; A61B 2090/374; A61B 2090/3937; A61B 2090/3954; A61B 5/0013; A61B 5/064; A61B 2090/3983; A61B 2090/3995; A61B 2090/3966; A61B 5/0263; A61N 2005/1055; A61N 2005/1051; G06K 2017/0045
See application file for complete search history.

(56) References Cited

U.S. PATENT DOCUMENTS

| | | | | |
|---|---|---|---|---|
| 6,292,683 | B1* | 9/2001 | Gupta | A61B 5/055 324/307 |
| 6,307,369 | B1* | 10/2001 | Felmlee | G01R 33/56509 324/307 |
| 6,771,068 | B2* | 8/2004 | Dale | G01R 33/56509 324/306 |
| 6,958,605 | B2* | 10/2005 | Dale | G01R 33/56509 324/306 |
| 7,127,092 | B2* | 10/2006 | Jack | A61B 5/055 382/128 |
| 7,245,124 | B2* | 7/2007 | Shu | G01R 33/54 324/307 |
| 7,432,706 | B2* | 10/2008 | van der Kouwe | G01R 33/4806 324/306 |
| 7,561,909 | B1* | 7/2009 | Pai | A61B 5/055 324/307 |
| 8,306,299 | B2* | 11/2012 | Samsonov | G01R 33/56509 382/128 |
| 8,624,596 | B2* | 1/2014 | Kannengiesser | G01R 33/5673 324/309 |
| 9,213,074 | B2* | 12/2015 | van der Kouwe | G01R 33/482 |
| 9,402,561 | B2* | 8/2016 | Krueger | A61B 5/055 |
| 2005/0036944 | A1* | 2/2005 | Van Den Brink | G01R 33/3415 424/9.3 |
| 2006/0226836 | A1* | 10/2006 | Shu | G01R 33/54 324/309 |
| 2017/0038448 | A1* | 2/2017 | Beck | G01R 33/56509 |

* cited by examiner

MR-BASED NAVIGATORS FOR INTER-SCAN AND INTRA-SCAN MOTION CORRECTION

TECHNOLOGY FIELD

The present invention relates generally to methods, systems, and apparatuses for using Magnetic Resonance (MR) navigators for inter-scan and intra-scan motion correction. The disclosed techniques may be applied, for example, in conjunction with automatic slice positioning techniques to provide accurate tracking of patient motion during MR scanning.

BACKGROUND

Automatic slice prescription techniques are nowadays commonly used during Magnetic Resonance Imaging (MM) scanning procedures. An anatomical localizer scan is acquired as the first scan of the session, and image processing techniques are used to determine a set of patient examination (frame-of-reference) specific anatomical references, for example, by identifying landmarks in the images. These anatomical references, which may contain geometric transformation matrices and body part boundary information, are stored in memory.

Based on the anatomical reference, the system automatically transforms subsequent atlas-related scan prescriptions into individual patient anatomy related slices and field-of-view prescriptions. This leads to more consistent field-of-view (FOV) placement and image orientations across patients and also ensures consistent FOV placements and image orientations for follow-up scans of the same patient. This technique has been implemented in similar fashion by various vendors (e.g., AutoAlign by Siemens, SmartExam by Philips, ReadyBrain by GE and NeuroLine/SpineLine by Toshiba) for imaging different anatomical region (e.g., brain, spine, knee etc.). FIG. 1 provides a schematic description of how, in practice, an anatomical localizer may be used for automatic FOV adjustment of subsequent scans based on anatomic landmark detection.

If the patient moves at any stage after the anatomical localizer is acquired the (frame-of-reference related) anatomical references are no longer valid and FOV placement for all subsequent scans after the motion occurs is inconsistent. FIG. 2 illustrates this inconsistency. As shown in this example, the patient motion after scan 1 makes FOV placement for scans 2 to N inconsistent since the anatomic landmarks calculated from the anatomical localizer are no longer valid. In some instances, automatic correction of the positioning throughout the scan session can also be used to ensure that when the technician places an ROI (FOV) on the initial localizer (3-plane or volume), it remains valid even if the patient moved since the localizer was acquired. The localizer doesn't have to be reacquired in such a case, but the positioning should be corrected for the intervening motion since that time so that the FOV is still as intended by the technician based on anatomy.

In conventional systems, patient motion is addressed by discontinuing the current frame-of-reference and to clear the memory of all anatomical references. Then, the localizer with the auto-detection of anatomical references has to be repeated and all slice prescriptions in the remaining scans have to be updated before finishing the examination. Any geometric relation between the two frame-of-references is lost. This approach has major disadvantages. First, the decision to re-run the anatomical localizer scan is taken by the operator whenever patient motion is observed e.g. with a monitoring camera. This is a not a foolproof method since small patient motions are difficult to spot, and depending on the setup there may not be a line of sight vision to the anatomy being scanned. The second disadvantage is that the anatomical localizer scan typically takes quite a long time so repeating this between scans is not efficient in clinical routine. Finally, with the conventional technique, it is difficult to overlay images acquired before and after this update as their geometrical relation is wrong. In some applications, this may, in turn, require a reacquisition of multiple series or of the whole examination.

SUMMARY

Embodiments of the present invention address and overcome one or more of the above shortcomings and drawbacks, by providing methods, systems, and apparatuses related to the use of magnetic resonance-based navigators for inter-scan and intra-scan motion correction. More specifically, a reference navigator is acquired immediately after the anatomical localizer scan. Before each subsequent scan the same navigator is acquired and compared with the reference navigator. The patient motion between scans is then estimated from this comparison.

According to some embodiments, a method for using navigators for inter-scan motion correction during imaging of a subject with a magnetic resonance imaging device includes performing (i) an anatomical localizer scan of a region of interest within the subject to identify one or more anatomical landmarks defining orientation of a surrounding field-of-view in the region of interest; (ii) an inter-scan motion reference scan of the region of interest to acquire a reference inter-scan dataset indicating a location of a reference navigator in the region of interest; and (iii) scans of the region of interest within the subject to acquire k-space data. The reference navigator may be, for example, a k-space navigator, an image space navigator, a 3D EPI based navigator, a Simultaneous Multi Slice (SMS) EPI navigator, or a sub-volume navigator. Prior to one or more of the scans, a motion correction process is performed. This process includes performing an inter-scan motion tracking scan to acquire a tracking inter-scan dataset indicating an updated location of the reference navigator in the region of interest; determining an estimation of inter-scan patient motion based on a comparison between the reference inter-scan dataset and the tracking inter-scan dataset; and updating the field-of-view relative to the one or more anatomical landmarks in the region of interest based on the estimation of inter-scan patient motion. Images of the region of interest may then be generated using the k-space data acquired with each of the plurality of scans.

Various enhancements, modifications, and other refinements may be applied to the aforementioned method in different embodiments of the present invention. For example, in some embodiments, this inter-scan motion reference scan is the anatomical localizer scan. In other embodiments, the inter-scan motion reference scan is performed immediately following the anatomical localizer scan. The comparison between the reference inter-scan dataset and the tracking inter-scan dataset performed during the method may include performing a registration of a first image corresponding to the reference inter-scan dataset and a second image corresponding to the tracking inter-scan dataset. In some embodiments, the tracking inter-scan dataset is a sub-volume of a subsequent scan. If the estimation of inter-scan patient motion exceeds a threshold value, a re-shimming of the magnetic resonance imaging device may be performed prior to performing a subsequent scan included in the plurality of scans.

Additionally, in some embodiments of the aforementioned method, the method further includes acquiring (i) a reference intra-scan dataset indicating a location of an intra-scan navigator in the region of interest and (ii) acquiring one or more tracking intra-scan datasets indicating an updated intra-scan location of the intra-scan navigator in the region of interest. Next, intra-scan motion correction may be performed on images corresponding to the scan based on a comparison of the reference intra-scan dataset and the one or more tracking intra-scan datasets. In some embodiments, the reference navigator corresponds to a first type of navigator and the intra-scan navigator corresponds to a second type of navigator.

According to another aspect of the present invention, a method for using navigators for inter-scan motion correction during imaging of a subject includes defining orientation of a field-of-view within a region of interest within the subject and acquiring a reference inter-scan dataset indicating a location of a reference navigator in the region of interest. Next, a plurality of scans of the region of interest is performed with a magnetic resonance imaging device to acquire k-space data. Prior to one or more of the plurality of scans, a motion correction process is performed which includes (i) performing an inter-scan motion tracking scan with the magnetic resonance imaging device to acquire a tracking inter-scan dataset indicating an updated location of the reference navigator in the region of interest, (ii) applying a transformation to the field-of-view based on differences between the reference inter-scan dataset and the tracking inter-scan dataset, and (iii) performing a re-shimming of the magnetic resonance imaging device. One or more images of the region of interest may then be generated using the k-space data acquired with each of the plurality of scans.

According to another aspect of the present invention, a system for using navigators for inter-scan motion correction during imaging of a subject includes an MRI scanner and an imaging computer. The MRI scanner is configured to (i) perform an anatomical localizer scan of a region of interest within the subject to identify one or more anatomical landmarks defining orientation of a surrounding field-of-view in the region of interest, (ii) perform an inter-scan motion reference scan of the region of interest to acquire a reference inter-scan dataset indicating a location of a reference navigator in the region of interest; (iii) perform a plurality of scans of the region of interest within the subject to acquire k-space data. Prior to one or more of the plurality of scans, the MRI scanner performs an inter-scan motion tracking scan to acquire a tracking inter-scan dataset indicating an updated location of the reference navigator in the region of interest. The imaging computer is configured to adjust the field-of-view for acquiring each of the plurality of scans based on differences between the reference inter-scan dataset and the tracking inter-scan dataset acquired immediately preceding the scan.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses related to using MR-based navigators for inter-scan and intra-scan motion correction. The motion correction techniques described herein enable independent tracking of inter scan and intra-scan motion, which provides flexibility in sequence design. Motion correction with MR-based navigators is generally more efficient than conventional systems because the acquisition time for MR-based navigators is much shorter (approximately 30-300 ms) than the anatomical localizer (many seconds). The disclosed techniques are also more robust than conventional motion correction systems because they are automated and do not rely on the operator monitoring the patient to detect motion. Additionally, using MR-based navigators for motion correction allows all the scans acquired during the MR examination to be in the same anatomically consistent frame of reference independent of subject motion during the entire examination. This, in turn, simplifies and speeds-up workflow in the radiology reading room and increases the efficiency of radiologists.

Figure 1:
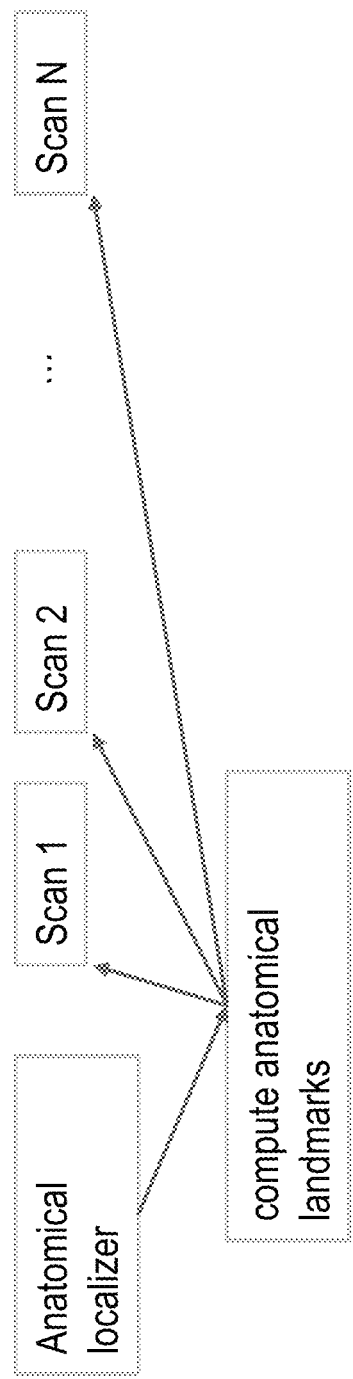
FIG. 1 provides an example scan sequence used for detecting anatomical references in conventional slice prescription techniques.
Figure 2:
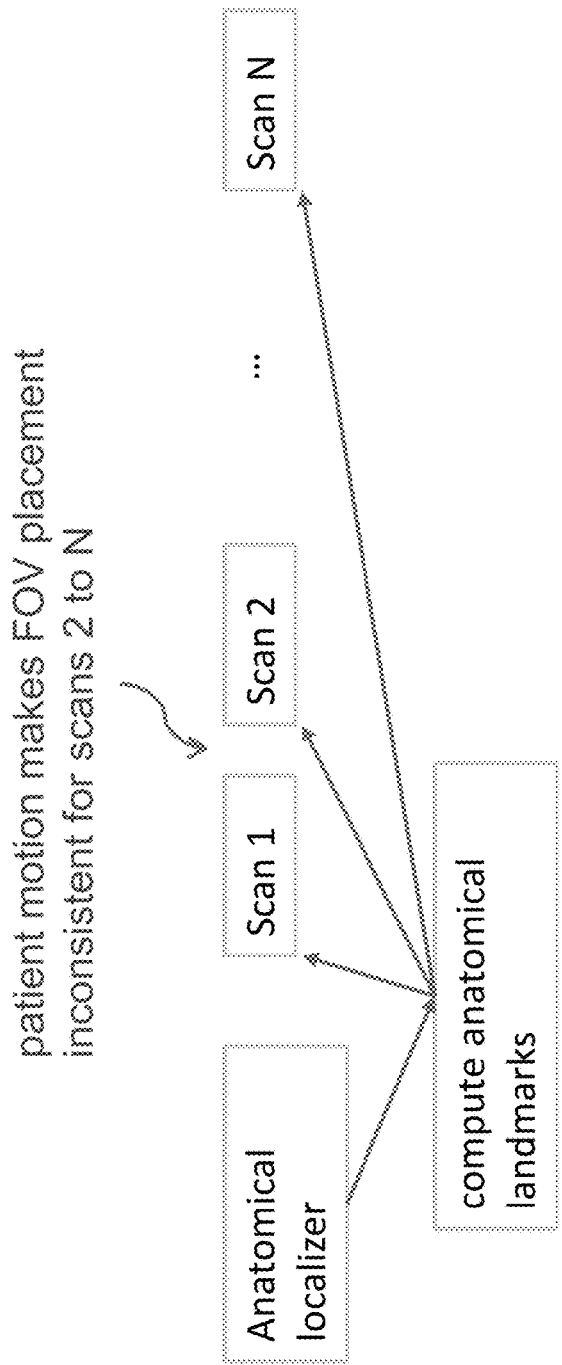
FIG. 2 illustrates how the scan sequence shown in FIG. 1 fails to provide accurate anatomical references and inconsistent FOV placement if a patient moves during scanning.
Figure 3:
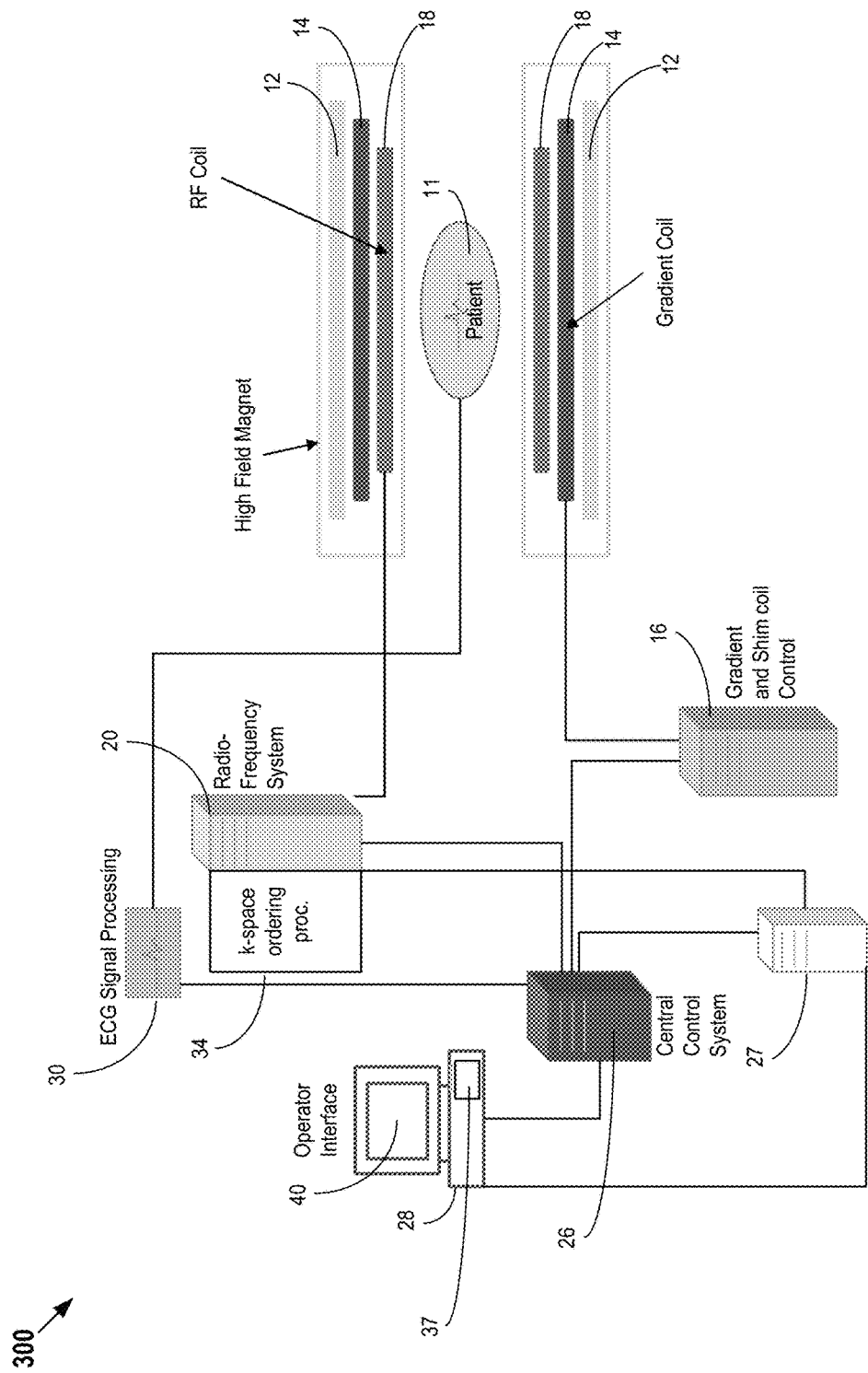
FIG. 3 shows a system for ordering acquisition of frequency domain components representing magnetic resonance image data for storage in a k-space storage array, as used by some embodiments of the present invention.

FIG. 3 shows a system 300 for ordering acquisition of frequency domain components representing MRI data for storage in a k-space storage array, as used by some embodiments of the present invention. In system 300, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MM device magnetic field resulting from patient anatomical variation and other sources. The magnetic field gradients include a slice-selection gradient magnetic field, a phase-encoding gradient magnetic field and a readout gradient magnetic field that are applied to patient 11.

Further, radio frequency (RF) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives magnetic resonance signals, i.e., signals from the excited protons within the body as they return to an equilibrium position established by the static and gradient magnetic fields. The magnetic resonance signals are detected and processed by a detector within RF module 20 and k-space component processor unit 34 to provide a magnetic resonance dataset to an image data processor for processing into an image. In some embodiments, the image data processor is located in central control unit 26. However, in other embodiments such as the one depicted in FIG. 3, the image data processor is located in a separate unit 27. Electrocardiogram (ECG) synchronization signal generator 30 provides ECG signals used for pulse sequence and imaging synchronization. A two or three dimensional k-space storage array of individual data elements in k-space component processor unit 34 stores corresponding individual frequency components comprising a magnetic resonance dataset. The k-space array of individual data elements has a designated center and individual data elements individually have a radius to the designated center.

A magnetic field generator (comprising coils 12, 14, and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components is sequentially acquired during acquisition of a magnetic resonance dataset representing a magnetic resonance image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components is substantially minimized.

Central control unit 26 uses information stored in an internal database to process the detected magnetic resonance signals in a coordinated manner to generate high quality images of a selected slice(s) of the body (e.g., using the image data processor) and adjusts other parameters of system 300. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Continuing with reference to FIG. 3, display processor 37 processes the magnetic resonance signals to reconstruct one or more images for presentation on display 40, for example. Various techniques may be used for reconstruction. For example, in some embodiments, an optimization algorithm is applied to iteratively solve a cost function which results in the reconstructed image.

The system 300 shown in FIG. 3 may be adapted using the techniques described herein to measure inter-scan patient motion using navigators. The measured motion can then be used to update FOV placement on subsequent scans after the motion occurs. The term "navigator," as used herein, refers to RF tracking pulses used to detect biological motion in the patient (e.g., motion resulting from breathing processes, blood flow processes, or patient shifts in position). MR-based navigators are well known in the field for motion correction within a scan (intra-scan motion correction). There are many possible navigator types including, without limitation, 1/2/3 dimensional k-space navigators and 1/2/3 dimensional image space navigators. It should also be noted that, in some embodiments, the position information can alternatively come from an external tracking device (e.g., a video and depth sensor), rather than through the use of a navigator.

Typically, navigators are used to correct for motion occurring within each scan (i.e., intra-scan motion correction). A reference navigator is collected at the beginning of the scan, and then, at regular intervals during the scan, the same navigators are acquired again. By comparing these subsequent navigators with the reference acquired at the beginning of the scan, subject motion is estimated and corrected for by adjusting the scanner coordinates on the fly (i.e., prospective motion correction).

As described herein, navigators are used in various embodiments for inter-scan and intra-scan motion correction in conjunction with automatic slice positioning techniques. Briefly, a reference navigator is acquired immediately after the anatomical localizer scan. Before each subsequent scan, the same navigator is acquired and compared with the reference navigator. For image-based navigators, the comparison of the navigators includes a registration between the reference and subsequent navigator images. The patient motion between scans is estimated from this comparison/registration step.

The motion estimate acquired using the technique described above can be used in at least two different ways. First, the estimate can be applied to the anatomical landmarks in order to update the landmarks and keep them consistent with the actual position of the patient. Thus, once the landmarks are acquired (e.g., through manual selection by the technician or using AutoAlign or a similar technique), they can be updated accordingly. Secondly, the estimate can be directly applied to the FOV of the subsequent scan after the anatomical landmark based transform is applied. Both techniques have the same goal which is to ensure that the subsequent scan is prescribed with a FOV which is anatomically consistent in spite of patient motion between scans.

Figure 4:
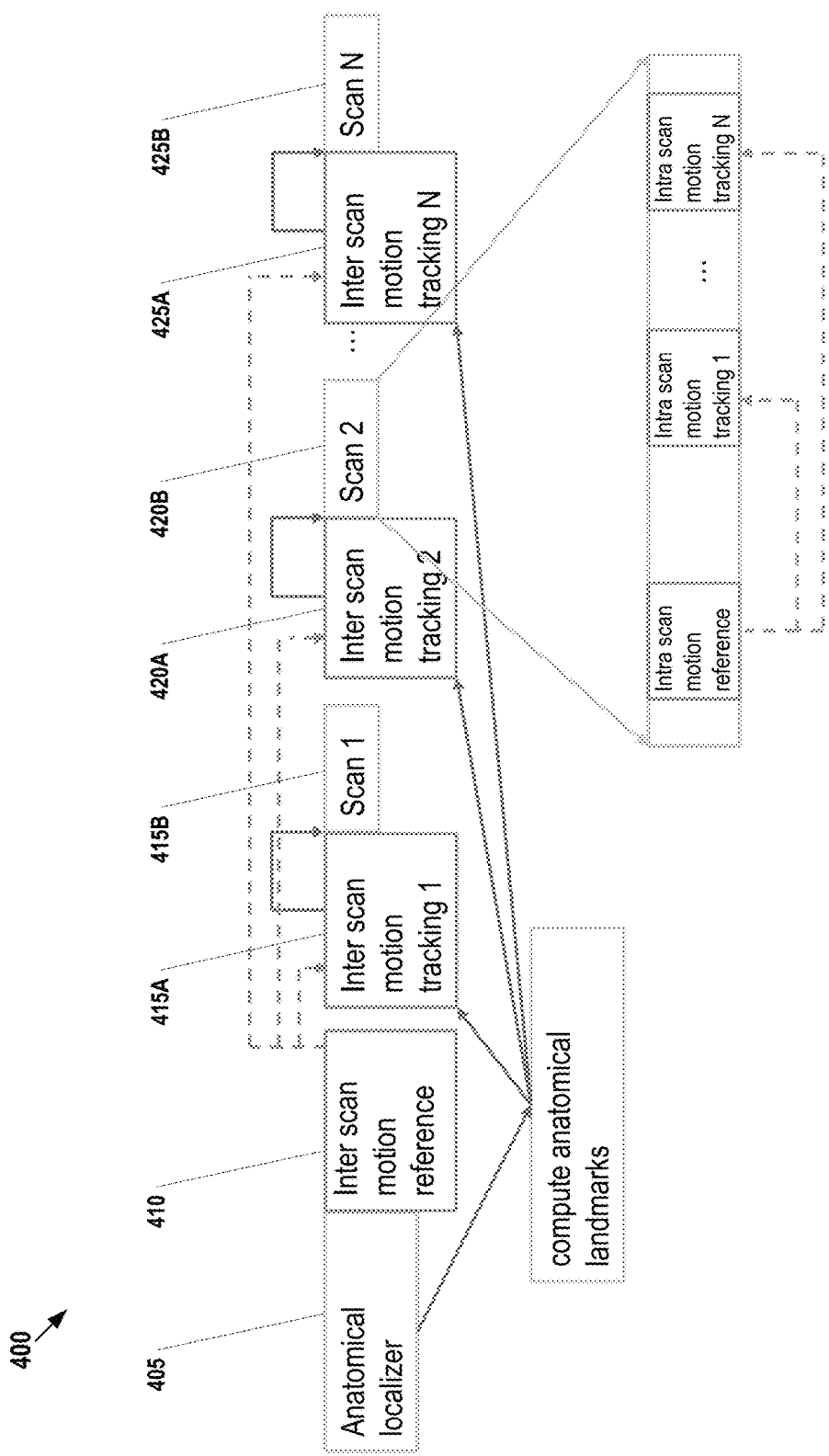
FIG. 4 illustrates how inter-scan and intra-scan motion correction may be performed, according to some embodiments.

FIG. 4 provides a process 400 for using navigators for inter-scan and intra-scan motion correction, according to some embodiments. In this example, an inter-scan motion reference scan 410 inserted after the anatomical localizer 405, and inter-scan motion tracking scans 415A, 420A, 425A are inserted before each subsequent scan 415B, 420B, 425B to update the automatic FOV in case of subject motion.

Additionally, the inter-scan motion reference scan 410 and inter-scan motion tracking scans 415A, 420A, 425A correct for motion within each scan. Motion transforms generated by the anatomic landmarks, inter-scan motion tracking, and inter-scan motion tracking are all combined to maintain consistency with the anatomic landmarks in spite of patient motion at any point during the examination. The inter-scan motion reference can optionally be identical to the inter-scan motion tracking volume. This has the advantage, that it is not necessary to acquire two navigators very close to each other in time.

Various MR based navigators can be used for this application. The main restriction is that the acquisition time for the navigator should be short so that it does not add too much time to the examination. For example, in some embodiments, a 3D Echo-planar imaging (EPI) based navigator such as a volume navigator (vNAV) may be used. As is generally known in the art, such navigators can acquire a low spatial resolution brain volume in approximately 300 msec. In other embodiments, a Simultaneous Multi Slice (SMS) EPI navigator is used, which can acquire a brain volume in approximately 30 msec. In other embodiments, sub-volume navigators may be employed, with or without SMS. Sub-volume navigators are described in detail in U.S. patent application Ser. No. 14/819,709, filed Aug. 6, 2015 and entitled "Method and Apparatus for Prospective Motion Correction Using Volume Navigators in Magnetic Resonance Imaging," which is hereby incorporated by reference in its entirety.

In some embodiments of the present invention, inter-scan and intra-scan motion tracking are combined. More specifically, motion transforms generated by the inter-scan and intra-scan navigators can be combined to correct for both inter-scan and intra-scan motion. This separation of inter and intra-scan motion tracking enables the uses of different navigator schemes to track these two motions. This is important since the intra-scan motion tracking navigator may change based on the type of sequence. For example, a 3D navigator like the vNAV is more suited to 3D sequences like Magnetization Prepared Rapid Gradient-Echo (MP-RAGE) or T2-weighted Sampling Perfection with Application optimized Contrasts using different flip angle Evolution (T2-SPACE). Conversely, a 2D navigator like the SMS-EPI navigator is more suited for 2D sequences like diffusion, turbo spin echo, etc. Typically a 2D SMS navigator might be well matched in terms of spin history to a 2D SMS sequence, and a one-slice-per-shot (truly 2D) navigator would be well matched to a 2D sequence.

In some embodiments, the motion transforms generated by automatic slice and FOV prescriptions, inter-scan motion tracking, and intra-scan motion tracking are all combined with the goal of maintaining consistency with the frame-of-reference in spite of patient motion at any point during the examination.

Figure 5:
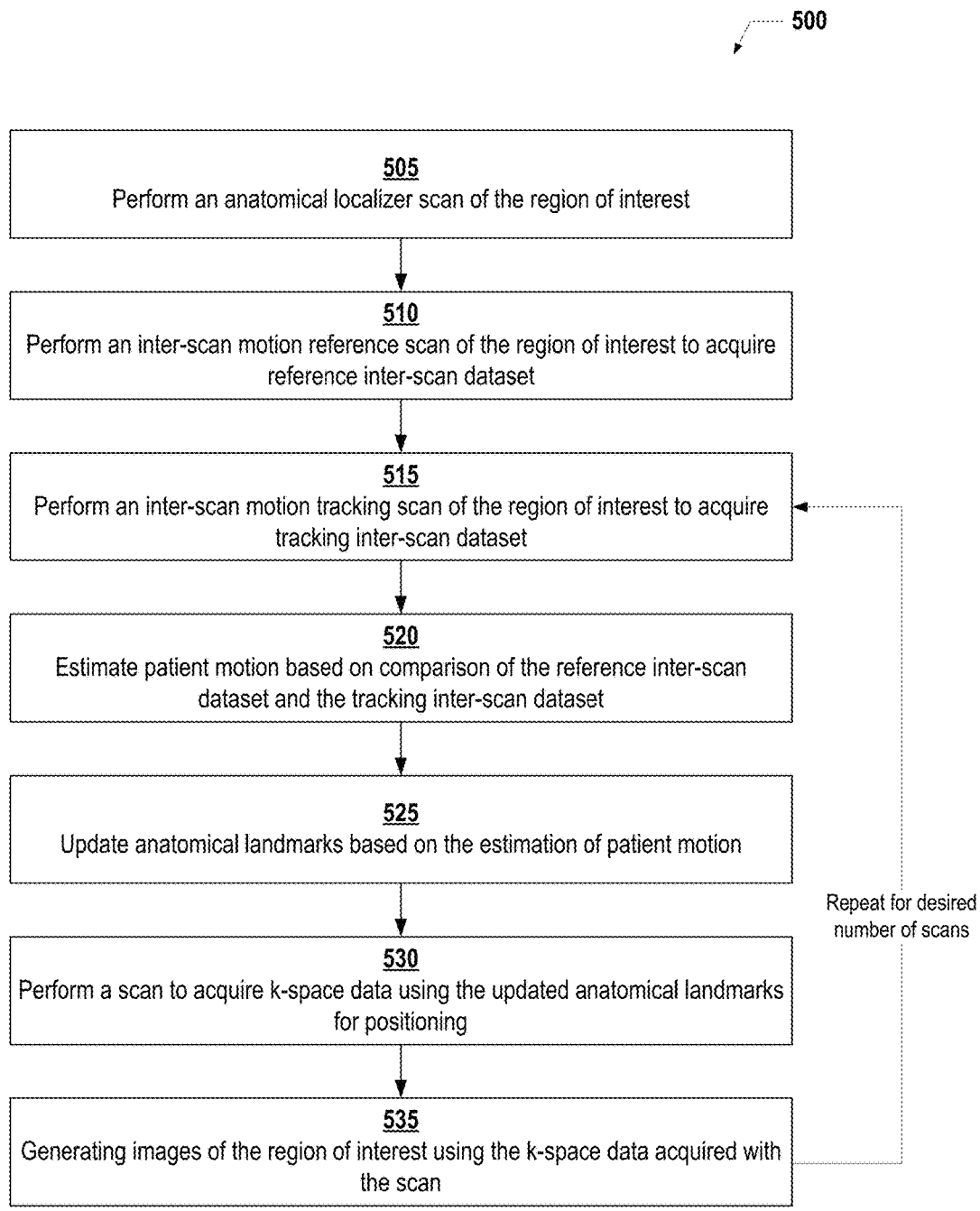
FIG. 5 provides an example for using navigators for inter-scan and intra-scan motion correction during MR imaging of a subject, according to some embodiments.

FIG. 5 provides an example method 500 for using navigators for inter-scan and intra-scan motion correction during MR imaging of a subject, according to some embodiments. Starting at step 505, an anatomical localizer scan of a region of interest within the subject is performed to identify one or more anatomical landmarks in the region of interest. Then, at step 510, an inter-scan motion reference scan of the region of interest is performed to acquire a reference inter-scan dataset indicating a location of a reference navigator in the region of interest. The reference navigator can generally be any navigator generally known in the art, including k-space or image space navigators. Example of reference navigators that may be used for tracking include, without limitation, 3D EPI based navigators, SMS EPI navigators, and sub-volume navigators.

In some embodiments, the inter-scan motion reference scan is performed during the anatomical localizer scan. That is, during acquisition of the anatomical landmarks, the reference navigators are also acquired. In other embodiments, the inter-scan motion reference scan is performed immediately following the anatomical localizer scan. "Immediately" in this context means as a soon as possible. The scanner may require some setup prior to performing the reference scan (e.g., to load components, perform shimming, etc.); however, the inter-scan motion reference scan should take place after that setup without any additional delay.

During steps 515-530 a plurality of scans are performed to acquire k-space data which is motion corrected. At step 515, an inter-scan motion tracking scan is performed to acquire a tracking inter-scan dataset which indicates an updated location of the reference navigator in the region of interest. Next, at step 520, the reference inter-scan dataset and the tracking inter-scan dataset are compared to determine an estimation of inter-scan patient motion. At step 525, the anatomical landmarks in the region of interest are updated based on the estimation of inter-scan patient motion. This updating may be performed using anatomical landmark-based registration techniques generally known in the art and may vary according to the type of data being used for comparison. For example, in some embodiments, an image corresponding to the reference inter-scan dataset is registered to an image corresponding to the tracking inter-scan dataset using image registration techniques known in the art (e.g., using rigid or affine transformations of the images).

In some embodiments, a change in patient position may be used to trigger re-shimming of the scanner. As is generally understood in the art, shimming is the process by which the main magnetic field ($B_0$) of the scanner is made more homogenous. This process is performed prior to scanning by making small adjustments to currents passing through gradients and higher order shim coils to optimize $B_0$ field homogeneity. As the patient moves, the magnetic field changes, and re-shimming is necessary. Thus, in some embodiments, if an inter-scan motion tracking scan detects patient motion with respect to the reference scan, re-shimming may be performed. In some instances, re-shimming may be triggered based on any patient motion. Alternatively, a threshold value may be set (e.g., one centimeter) and re-shimming is triggered if a reference point moves beyond the threshold value. To deal with the possibility of motion during/after the shim, in some embodiments, the navigator-shim scans are repeated until the two navigators in the last navigator-shim-navigator set match one another.

Continuing with reference to FIG. 5, at step 530, a scan is performed to acquire k-space data using the updated anatomical landmarks for positioning. During each scan, intra-scan motion correction may be performed using techniques which are similar to those employed for inter-scan motion correction. For example, a reference intra-scan dataset may be acquired which indicates a location of an intra-scan navigator in the region of interest. One or more tracking intra-scan dataset may then be acquired which indicate an updated intra-scan location of the intra-scan navigator in the region of interest. Then, intra-scan motion correction may be performed on images corresponding to the scan based on a comparison of the first intra-scan dataset and the one or more second intra-scan datasets. The navigator used for intra-scan motion correction may be the same navigator used for inter-scan motion correction or, in some instances, inter-scan motion correction and intra-scan motion correction may utilize different types of navigators.

Finally, at step 535, one or more images of the region of interest are generated by reconstructing the k-space data acquired with the scan performed at step 530. In some embodiments, rather than interleaving image reconstruction in the loop (i.e., between scans), reconstruction for the acquired datasets could be deferred until after all the acquisitions are complete. Steps 515-535 are repeated for the desired number of scans (e.g., as specified by the operator or the protocol).

Figure 6:
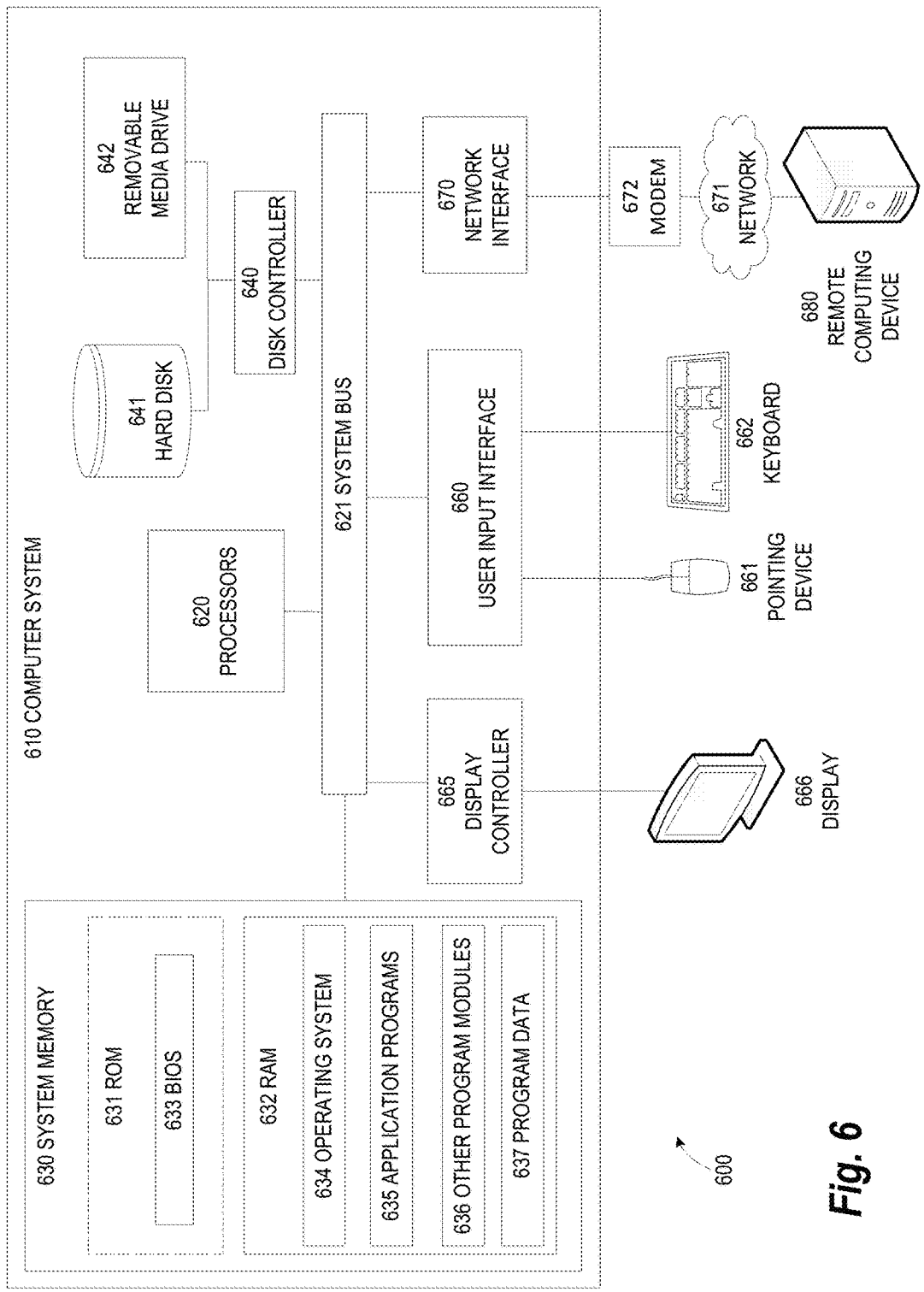
FIG. 6 illustrates an exemplary computing environment within which embodiments of the invention may be implemented.

FIG. 6 illustrates an exemplary computing environment 600 within which embodiments of the invention may be implemented. For example, this computing environment 600 may be used to implement the process 500 described in FIG. 5 and/or one or more of the components illustrated in the system 300 of FIG. 3. The computing environment 600 may include computer system 610, which is one example of a computing system upon which embodiments of the invention may be implemented. Computers and computing environments, such as computer system 610 and computing environment 600, are known to those of skill in the art and thus are described briefly here.

As shown in FIG. 6, the computer system 610 may include a communication mechanism such as a bus 621 or other communication mechanism for communicating information within the computer system 610. The computer system 610 further includes one or more processors 620 coupled with the bus 621 for processing the information. The processors 620 may include one or more central processing units (CPUs), graphical processing units (GPUs), or any other processor known in the art.

The computer system 610 also includes a system memory 630 coupled to the bus 621 for storing information and instructions to be executed by processors 620. The system memory 630 may include computer readable storage media in the form of volatile and/or nonvolatile memory, such as read only memory (ROM) 631 and/or random access memory (RAM) 632. The system memory RAM 632 may include other dynamic storage device(s) (e.g., dynamic RAM, static RAM, and synchronous DRAM). The system memory ROM 631 may include other static storage device(s) (e.g., programmable ROM, erasable PROM, and electrically erasable PROM). In addition, the system memory 630 may be used for storing temporary variables or other intermediate information during the execution of instructions by the processors 620. A basic input/output system (BIOS) 633 containing the basic routines that help to transfer information between elements within computer system 610, such as during start-up, may be stored in ROM 631. RAM 632 may contain data and/or program modules that are immediately accessible to and/or presently being operated on by the processors 620. System memory 630 may additionally include, for example, operating system 634, application programs 635, other program modules 636 and program data 637.

The computer system 610 also includes a disk controller 640 coupled to the bus 621 to control one or more storage devices for storing information and instructions, such as a hard disk 641 and a removable media drive 642 (e.g., floppy disk drive, compact disc drive, tape drive, and/or solid state drive). The storage devices may be added to the computer system 610 using an appropriate device interface (e.g., a small computer system interface (SCSI), integrated device electronics (IDE), Universal Serial Bus (USB), or FireWire).

The computer system 610 may also include a display controller 665 coupled to the bus 621 to control a display 666, such as a cathode ray tube (CRT), liquid crystal display (LCD) or light-emitting diode (LED), for displaying information to a computer user. The computer system includes an input interface 660 and one or more input devices, such as a keyboard 662 and a pointing device 661, for interacting with a computer user and providing information to the processor 620. The pointing device 661, for example, may be a mouse, a trackball, or a pointing stick for communicating direction information and command selections to the processor 620 and for controlling cursor movement on the display 666. The display 666 may provide a touch screen interface which allows input to supplement or replace the communication of direction information and command selections by the pointing device 661.

The computer system 610 may perform a portion or all of the processing steps of embodiments of the invention in response to the processors 620 executing one or more sequences of one or more instructions contained in a memory, such as the system memory 630. Such instructions may be read into the system memory 630 from another computer readable medium, such as a hard disk 641 or a removable media drive 642. The hard disk 641 may contain one or more datastores and data files used by embodiments of the present invention. Datastore contents and data files may be encrypted to improve security. The processors 620 may also be employed in a multi-processing arrangement to execute the one or more sequences of instructions contained in system memory 630. In alternative embodiments, hard-wired circuitry may be used in place of or in combination with software instructions. Thus, embodiments are not limited to any specific combination of hardware circuitry and software.

As stated above, the computer system 610 may include at least one computer readable medium or memory for holding instructions programmed according to embodiments of the invention and for containing data structures, tables, records, or other data described herein. The term "computer readable medium" as used herein refers to any medium that participates in providing instructions to the processor 620 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 641 or removable media drive 642. Non-limiting examples of volatile media include dynamic memory, such as system memory 630. Non-limiting examples of transmission media include coaxial cables, copper wire, and fiber optics, including the wires that make up the bus 621. Transmission media may also take the form of acoustic or light waves, such as those generated during radio wave and infrared data communications.

The computing environment 600 may further include the computer system 610 operating in a networked environment using logical connections to one or more remote computers, such as remote computer 680. Remote computer 680 may be a personal computer (laptop or desktop), a mobile device, a server, a router, a network PC, a peer device or other common network node, and typically includes many or all of the elements described above relative to computer system 610. When used in a networking environment, computer system 610 may include modem 672 for establishing communications over a network 671, such as the Internet. Modem 672 may be connected to bus 621 via user network interface 670, or via another appropriate mechanism.

Network 671 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 610 and other computers (e.g., remote computer 680). The network 671 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 671.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method for using navigators for inter-scan motion correction during imaging of a subject with a magnetic resonance imaging device, the method comprising:
performing an anatomical localizer scan of a region of interest within the subject to identify one or more anatomical landmarks defining orientation of a surrounding field-of-view in the region of interest;
performing an inter-scan motion reference scan of the region of interest to acquire a reference inter-scan dataset indicating a location of a reference navigator in the region of interest;
performing a plurality of scans of the region of interest within the subject to acquire k-space data, wherein, prior to one or more of the plurality of scans, a motion correction process is performed comprising:
performing an inter-scan motion tracking scan to acquire a tracking inter-scan dataset indicating an updated location of the reference navigator in the region of interest,
determining an estimation of inter-scan patient motion based on a comparison between the reference inter-scan dataset and the tracking inter-scan dataset, and
updating the field-of-view relative to the one or more anatomical landmarks in the region of interest based on the estimation of inter-scan patient motion; and
generating one or more images of the region of interest using the k-space data acquired with each of the plurality of scans.

2. The method of claim 1, wherein the inter-scan motion reference scan is the anatomical localizer scan.

3. The method of claim 1, wherein the inter-scan motion reference scan is performed immediately following the anatomical localizer scan.

4. The method of claim 1, wherein the comparison between the reference inter-scan dataset and the tracking inter-scan dataset comprises performing a registration of a first image corresponding to the reference inter-scan dataset and a second image corresponding to the tracking inter-scan dataset.

5. The method of claim 1, wherein the reference navigator is a k-space navigator.

6. The method of claim 1, wherein the reference navigator is an image space navigator.

7. The method of claim 1, wherein the reference navigator is a 3D EPI based navigator.

8. The method of claim 1, wherein the reference navigator is a Simultaneous Multi Slice (SMS) EPI navigator.

9. The method of claim 1, wherein the reference navigator is a sub-volume navigator.

10. The method of claim 1, wherein the tracking inter-scan dataset is a sub-volume of a subsequent scan.

11. The method of claim 1, further comprising:
acquiring a reference intra-scan dataset indicating a location of an intra-scan navigator in the region of interest;
acquiring one or more tracking intra-scan datasets indicating an updated intra-scan location of the intra-scan navigator in the region of interest;
performing intra-scan motion correction on images corresponding to the scan based on a comparison of the reference intra-scan dataset and the one or more tracking intra-scan datasets.

12. The method of claim 11, wherein the reference navigator corresponds to a first type of navigator and the intra-scan navigator corresponds to a second type of navigator.

13. The method of claim 1, further comprising:
if the estimation of inter-scan patient motion exceeds a threshold value, performing a re-shimming of the magnetic resonance imaging device prior to performing a subsequent scan included in the plurality of scans.

14. A method for using navigators for inter-scan motion correction during imaging of a subject, the method comprising:
defining orientation of a field-of-view within a region of interest within the subject;
acquiring a reference inter-scan dataset indicating a location of a reference navigator in the region of interest;
performing a plurality of scans of the region of interest with a magnetic resonance imaging device to acquire k-space data, wherein, prior to one or more of the plurality of scans, a motion correction process is performed comprising:
performing an inter-scan motion tracking scan with the magnetic resonance imaging device to acquire a tracking inter-scan dataset indicating an updated location of the reference navigator in the region of interest,
applying a transformation to the field-of-view based on differences between the reference inter-scan dataset and the tracking inter-scan dataset, and
performing a re-shimming of the magnetic resonance imaging device; and
generating one or more images of the region of interest using the k-space data acquired with each of the plurality of scans.

15. The method of claim 14, wherein the comparison between the reference inter-scan dataset and the tracking inter-scan dataset comprises performing a registration of a first image corresponding to the reference inter-scan dataset and a second image corresponding to the tracking inter-scan dataset.

16. The method of claim 14, wherein the reference navigator is a k-space navigator.

17. The method of claim 14, wherein the reference navigator is an image space navigator.

18. The method of claim 14, wherein the reference navigator is a 3D EPI based navigator.

19. The method of claim 14, wherein the reference navigator is a Simultaneous Multi Slice (SMS) EPI navigator.

20. The method of claim 14, wherein the reference navigator is a sub-volume navigator.

21. A system for using navigators for inter-scan motion correction during imaging of a subject, the system comprising:
an MRI scanner configured to:
perform an anatomical localizer scan of a region of interest within the subject to identify one or more anatomical landmarks defining orientation of a surrounding field-of-view in the region of interest,
perform an inter-scan motion reference scan of the region of interest to acquire a reference inter-scan dataset indicating a location of a reference navigator in the region of interest;
perform a plurality of scans of the region of interest within the subject to acquire k-space data, and
prior to one or more of the plurality of scans, perform an inter-scan motion tracking scan to acquire a tracking inter-scan dataset indicating an updated location of the reference navigator in the region of interest; and
an imaging computer configured to adjust the field-of-view for acquiring each of the plurality of scans based on differences between the reference inter-scan dataset and the tracking inter-scan dataset acquired immediately preceding the scan.

* * * * *